United States Patent
Kimball et al.

(10) Patent No.: US 10,722,633 B2
(45) Date of Patent: Jul. 28, 2020

(54) ENERGY MANAGEMENT OF BLOOD PUMP CONTROLLERS

(71) Applicant: TC1 LLC, St. Paul, MN (US)

(72) Inventors: Brian Kimball, Medford, MA (US); Joseph C. Stark, III, San Leandro, CA (US); Peter Thatcher, Benicia, CA (US); John Freddy Hansen, Pleasanton, CA (US); Peter Andriola, Dublin, CA (US); Carine Hoarau, Lafayette, CA (US); Jaime Arturo Romero, San Leandro, CA (US); Jesse Gage, Los Altos Hills, CA (US)

(73) Assignee: TC1 LLC, St. Paul, MN (US)

( * ) Notice: Subject to any disclaimer, the term of this patent is extended or adjusted under 35 U.S.C. 154(b) by 150 days.

(21) Appl. No.: 15/972,909

(22) Filed: May 7, 2018

(65) Prior Publication Data

US 2018/0250459 A1  Sep. 6, 2018

Related U.S. Application Data (63) Continuation of application No. PCT/US2016/062740, filed on Nov. 18, 2016.
(Continued)

(51) Int. Cl.
*A61M 1/12* (2006.01)
*A61M 1/10* (2006.01)
(Continued)

(52) U.S. Cl.
CPC .......... *A61M 1/127* (2013.01); *A61M 1/1086* (2013.01); *A61M 1/122* (2014.02);
(Continued)

(58) Field of Classification Search
CPC .... A61M 1/127; A61M 1/122; A61M 1/1086; A61M 2205/3368; A61M 2205/3523;
(Continued)

(56) References Cited

U.S. PATENT DOCUMENTS 3,882,861 A  5/1975  Kettering et al.
4,521,871 A  6/1985  Galdun et al.
(Continued)

FOREIGN PATENT DOCUMENTS

EP  1 812 094 A  5/2006
WO  2006/055745 A2  5/2006
(Continued)

OTHER PUBLICATIONS

Heartmate II , "The HeartMate II system", HeartMate II, Left Ventricular Assist System, Retrieved from Internet : http://heartmateii.com/heartmate-ii-system.aspx, Jul. 16, 2015, 2 pages.
(Continued)

*Primary Examiner* — Paula J Stice
(74) *Attorney, Agent, or Firm* — Kilpatrick Townsend & Stockton LLP (57) ABSTRACT

Systems and related methods for supplying power to a medical device employ self-charging serially-connectable portable batteries. A system includes a base module and external battery modules. The base module is operatively coupled with the medical device and includes a base module input connector. Each of the external battery modules includes one or more battery cells, an output connector, an input connector, and a controller. The output connector is configured to output electrical power from the external battery module. The input connector is configured to receive electrical power from another of the plurality of external battery modules. The controller is operatively coupled with the one or more battery cells, the output connector, and the
(Continued)

input connector. The controller is configured to control distribution of electrical power received via the input connector to charge the one or more battery cells and/or to be output via the output connector.

20 Claims, 4 Drawing Sheets

Related U.S. Application Data (60) Provisional application No. 62/257,894, filed on Nov. 20, 2015.

(51) Int. Cl.
  *H02J 7/00* (2006.01)
  *H02J 7/34* (2006.01)
  *G01R 31/382* (2019.01)

(52) U.S. Cl.
  CPC .............. *H02J 7/00* (2013.01); *H02J 7/0013* (2013.01); *H02J 7/0021* (2013.01); *H02J 7/34* (2013.01); *A61M 2205/3368* (2013.01); *A61M 2205/3523* (2013.01); *A61M 2205/3592* (2013.01); *A61M 2205/8206* (2013.01); *A61M 2205/8237* (2013.01); *A61M 2205/8262* (2013.01); *G01R 31/382* (2019.01)

(58) Field of Classification Search
  CPC .. A61M 2205/8206; A61M 2205/8237; A61M 2205/8262; H02J 7/00; H02J 7/0013; H02J 7/0021; H02J 7/34; G01R 31/382
  See application file for complete search history.

(56) References Cited

U.S. PATENT DOCUMENTS

| | | |
|---|---|---|
| 5,046,965 A | 9/1991 | Neese et al. |
| 5,695,474 A | 12/1997 | Daugherty |
| 5,888,242 A | 3/1999 | Antaki et al. |
| 5,935,105 A | 8/1999 | Manning et al. |
| 5,991,595 A | 11/1999 | Romano et al. |
| 6,071,093 A | 6/2000 | Hart |
| 6,116,862 A | 9/2000 | Rau et al. |
| 6,123,726 A | 9/2000 | Mori et al. |
| 6,146,179 A | 11/2000 | Denny et al. |
| 6,183,412 B1 | 2/2001 | Benkowski et al. |
| 6,234,772 B1 | 5/2001 | Wampler et al. |
| 6,264,635 B1 | 7/2001 | Wampler et al. |
| 6,494,736 B2 | 12/2002 | Mito et al. |
| 6,592,620 B1 | 7/2003 | Lancisi et al. |
| 6,688,861 B2 | 2/2004 | Wampler |
| 7,340,304 B2 | 3/2008 | MacDonald et al. |
| 7,425,142 B2 | 9/2008 | Putz et al. |
| 7,658,613 B1 | 2/2010 | Griffin et al. |
| 7,699,586 B2 | 4/2010 | Larose et al. |
| 7,961,156 B2 | 6/2011 | Knott et al. |
| 7,976,271 B2 | 7/2011 | Larose et al. |
| 7,997,854 B2 | 8/2011 | Larose et al. |
| 8,007,254 B2 | 8/2011 | Larose et al. |
| 8,029,441 B2 | 10/2011 | Mazza et al. |
| 8,152,493 B2 | 4/2012 | Larose et al. |
| 8,157,720 B2 | 4/2012 | Marseille et al. |
| 8,186,665 B2 | 5/2012 | Akema |
| 8,323,174 B2 | 12/2012 | Jeevanandam et al. |
| 8,344,847 B2 | 1/2013 | Moberg et al. |
| 8,348,678 B2 | 1/2013 | Hardisty et al. |
| 8,449,444 B2 | 5/2013 | Poirier |
| 8,506,471 B2 | 8/2013 | Bourque |
| 8,562,508 B2 | 10/2013 | Dague et al. |
| 8,597,350 B2 | 12/2013 | Rudser et al. |
| 8,628,460 B2 | 1/2014 | Yomtov et al. |
| 8,639,348 B2 | 1/2014 | Geheb |
| 8,652,024 B1 | 2/2014 | Yanai et al. |
| 8,657,733 B2 | 2/2014 | Ayre et al. |
| 8,668,473 B2 | 3/2014 | Larose et al. |
| 8,684,763 B2 | 4/2014 | White et al. |
| 8,894,561 B2 | 11/2014 | Callaway et al. |
| 8,971,958 B2 | 3/2015 | Frikart et al. |
| 9,302,035 B2 | 4/2016 | Flaherty et al. |
| 2002/0007198 A1 | 1/2002 | Haupert et al. |
| 2005/0071001 A1 | 3/2005 | Jarvik |
| 2007/0078293 A1 | 4/2007 | Shambaugh et al. |
| 2007/0142696 A1 | 6/2007 | Crosby et al. |
| 2008/0021394 A1 | 1/2008 | Larose et al. |
| 2009/0118827 A1 | 5/2009 | Sugiura |
| 2009/0203957 A1 | 8/2009 | Larose et al. |
| 2011/0218383 A1 | 9/2011 | Broen et al. |
| 2012/0046514 A1 | 2/2012 | Bourque |
| 2012/0095281 A1 | 4/2012 | Reichenbach et al. |
| 2012/0157755 A1* | 6/2012 | D'Ambrosio ......... A61M 1/127 600/16 |
| 2012/0172657 A1 | 7/2012 | Marseille et al. |
| 2012/0183261 A1 | 7/2012 | Schwandt et al. |
| 2013/0096364 A1 | 4/2013 | Reichenbach et al. |
| 2013/0121821 A1 | 5/2013 | Ozaki et al. |
| 2013/0127253 A1 | 5/2013 | Stark et al. |
| 2013/0170970 A1 | 7/2013 | Ozaki et al. |
| 2013/0225909 A1 | 8/2013 | Dormanen et al. |
| 2013/0314047 A1 | 11/2013 | Eagle et al. |
| 2014/0073838 A1 | 3/2014 | Dague et al. |
| 2014/0194985 A1 | 7/2014 | Vadala, Jr. |
| 2014/0243970 A1 | 8/2014 | Yanai |
| 2014/0309733 A1 | 10/2014 | Cotter et al. |
| 2015/0038771 A1 | 2/2015 | Marseille et al. |
| 2015/0120067 A1* | 4/2015 | Wing .................... H02J 7/0063 700/282 |
| 2016/0095968 A1 | 4/2016 | Rudser |
| 2018/0256796 A1 | 9/2018 | Hansen |
| 2018/0256800 A1 | 9/2018 | Conyers et al. |
| 2018/0256801 A1 | 9/2018 | Conyers et al. |

FOREIGN PATENT DOCUMENTS

| | | |
|---|---|---|
| WO | 2014107424 A2 | 7/2014 |
| WO | 2017087380 A1 | 5/2017 |
| WO | 2017087717 A1 | 5/2017 |
| WO | 2017087728 A1 | 5/2017 |

OTHER PUBLICATIONS

My Lvad, "Berlin Heart Incor", Retrieved from Internet:http://www.mylvad.com/content/berlin-heart-incor, Jul. 16, 2015, 3 pages.

* cited by examiner

ENERGY MANAGEMENT OF BLOOD PUMP CONTROLLERS

CROSS-REFERENCE TO RELATED APPLICATION

The present application is a Continuation of PCT/US2016/062740 filed Nov. 18, 2016; which claims priority to and benefit of U.S. Provisional Application No. 62/257,894, filed Nov. 20, 2015, the disclosure of which is incorporated herein by reference in its entirety for all purposes.

BACKGROUND

Ventricular assist devices, known as VADs, often include an implantable blood pump and are used for both short-term (i.e., days, months) and long-term applications (i.e., years or a lifetime) when a patient's heart is incapable of providing adequate circulation, commonly referred to as heart failure or congestive heart failure. According to the American Heart Association, more than five million Americans are living with heart failure, with about 670,000 new cases diagnosed every year. People with heart failure often have shortness of breath and fatigue. Years of living with blocked arteries and/or high blood pressure can leave a heart too weak to pump enough blood to the body. As symptoms worsen, advanced heart failure develops.

A patient suffering from heart failure may use a VAD while awaiting a heart transplant or as a long term destination therapy. A patient may also use a VAD while recovering from heart surgery. Thus, a VAD can supplement a weak heart (i.e., partial support) or can effectively replace the natural heart's function.

All ventricular assist systems (VAS) require several watts of power to provide cardiac support. Thus, patients using a ventricular assist system and their supporting caregivers or providers (hereinafter "users") can use non-implanted replenishable and/or replaceable power supplies to maintain mobility. Such non-implanted power supplies typically include battery packs and AC wall power converters. The power from these sources may be conveyed to the VAD via a VAS controller using cables.

Existing products, however, use several power cables or a single large enclosure containing both a power source and a VAS controller. The use of several power cables requires users to manage multiple cables. A single large enclosure is cumbersome to wear on the body owing to the relatively large size of batteries and other energy storage devices realizable using present-day technology.

Additionally, while using existing portable, wearable energy sources, users have limited options for expanding the amount of wearable energy storage with present commercial products. Instead, many existing products employ a single energy storage configuration, typically a battery of fixed capacity. Some existing devices allow for optional larger capacity battery packs to be used in lieu of a standard battery pack.

Finally, for all existing products, depleted energy sources must be disconnected before new energy sources can be connected. If a failure occurs with an energy storage system, rendering it inoperable, a user must disconnect the failed energy source before connecting another one. During this time, the medical device may not have been functional or functioning at a reduced capacity. Accordingly, improved portable energy supply systems and related methods that do not have at least some of the above-discussed disadvantages would provide benefits to users of wearable or implanted medical devices.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Embodiments of the invention described herein include energy supply systems for wearable or implantable medical devices, and related methods, that provide increase flexibility with regard to carried battery capacity and recharging of the carried battery capacity without having to disconnect batteries for recharging. In many embodiments, each of a plurality of external battery modules includes an input connector to receive electrical power and an output connector from which to output electrical power. The wearable or implantable medical device or a controller for the medical device can include an input connector that is connectable with the output connector of a first of the external battery modules. In many embodiments, the output connector of a second of the external battery modules is connectable with the input connector of the first of the external battery modules. The input connector of the second of the external battery modules can be connected with the output connector of a third of the external battery modules, and so on in a similar fashion so as to serially connect any desired suitable number of the external battery modules. In some embodiments, the number of the external battery modules that can be serially connected may be limited by software algorithms in the wearable or implantable medical device or the control unit of the medical device. At least where the wearable or implantable medical device or the controller of the medical device includes internal energy storage, the minimum number of connected external battery modules can be zero. In many embodiments, each of the external battery modules includes an integrated charger configured to recharge battery cell(s) of the external battery module. Each of the external battery modules can include a controller configured to monitor and communicate state of charge of the external battery module and/or to control recharging of the external battery module. Each of the external battery modules can communicate with the wearable or implantable medical device or a controller of the medical device so as to receive parameters used to control charging and discharging of the external battery module. Accordingly, users can add and remove external carried battery capacity in a flexible manner and the battery modules can be recharged without having to disconnect the battery modules.

Thus, in one aspect, a system is provided for supplying power to a medical device worn by a user or implanted in the user. The system includes a base module and a plurality of external battery modules. The base module is configured to be operatively coupled with the medical device to supply electrical power to the medical device. The base module includes a base module input connector. Each of the external battery modules includes one or more battery cells, an output connector, an input connector, and a controller. The one or more battery cells are configured to store electrical power. The output connector is configured to output electrical power from the external battery module. The input connector is configured to receive electrical power from another of the plurality of external battery modules. The controller is configured to control distribution of electrical power received via the input connector to charge the one or more battery cells and/or to be output via the output connector.

In many embodiments of the system, the base module includes one or more base module battery cells and base module controller. The base module battery cells are configured to store electrical power. The base module controller can be configured to control distribution of electrical power received via the base module input connector to charge the one or more base module battery cells and/or to be output to supply electrical power to the medical device.

In many embodiments, the system is configured to detect the configuration of connected external battery modules and control charging of the medical device, a controller of the medical device, and/or the connected external battery modules in accordance with the detected configuration of connected external battery modules. For example, each of: (1) the base module input connector, (2) the output connector of each of the plurality of external battery modules, and (3) the input connector of each of the plurality of external battery modules can include a data connection for transferring a connection signal to the base module controller and/or to the controller of another of the plurality of external battery modules indicating connection of one or more of the plurality of external battery modules. The base module controller can be configured to control the controller of each of the plurality of external battery modules via the data connection to control the distribution of electrical power received via the input connector of the external battery module to charge the one or more battery cells of the external battery module and/or to be output via the output connector of the external battery module. In many embodiments of the system, the plurality of external battery modules can be connected to the base module in a connection sequence order. The base module controller and the controller of each of the plurality of external battery modules can be configured to implement a charging sequence in which the base module is charged first and at least one of the plurality of external battery modules is charged in the connection sequence order. In many embodiments of the system, the data connection includes a fiber optic connector for connecting fiber optic data lines. A fiber optic data connection eliminates many electromagnetic interference considerations present in existing system.

In many embodiments of the system, the state of charge of the system is monitored and communicated. For example, the base module controller can be configured to monitor a base module charge level of the one or more base module battery cells. The base module controller can be configured to indicate the base module charge level to the user or a person other than the user. The base module can include a wireless transmitter to wirelessly transmit the base module charge level to an electronic device, such as a cellular/smart phone, tablet, computer, watch, etc., for communication to the user or a person other than the user (e.g., physician, family member, etc.). The controller of each of the plurality of external battery modules can be configured to monitor a charge level of the one or more battery cells of the external battery module and communicate the charge level to the base module controller. The base module controller can be configured to communicate the charge level of at least one of the plurality of external battery modules to the user or a person other than the user. The base module can include a wireless transmitter to wirelessly transmit the base module charge level and the charge level of each of at least one of the plurality of external battery modules to an electronic device for communication to the user or a person other than the user. Each of the plurality of external battery modules can include one or more indicators controlled by the respective controller to indicate the charge level of the one or more battery cells of the external battery module. In many embodiments of the system, the one or more indicators include visual indicators, such as one or more light emitting diodes (LEDs), audio indicators, or haptic indicators.

In many embodiments of the system, the input and the output connectors are configured to prevent orientation based misconnection. For example, each of the input connector and the output connector of each of the plurality of external battery modules and the base module input connector can include two ground line connectors and two power line connectors arranged in a linear array symmetrically on opposite sides of the data connection to accommodate connection of the input and output connectors in opposite orientations.

Connection of an external battery module can be detected via a voltage potential output from the external battery module. For example, each of the base module controller and the controller of each of the plurality of external battery modules can be configured to detect the connection of one or more of the plurality of external battery modules via a voltage potential applied to the base module input connector or the input connector of the external battery module, respectively.

In many embodiments, the system includes one or more electronic switches to control charging of the base module and/or the external battery modules. For example, the base module controller can include one or more electronic switches connected between the base module input connector and the one or more base module battery cells to control charging of the one or more base module battery cells via electrical power received via the base module input connector. The controller of each of the plurality of external battery modules can include one or more electronic switches connected between the input connector and the one or more battery cells of the external battery module to control charging of the one or more battery cells via electrical power received via the input connector.

In many embodiments, the system is configured to control charging rate(s) for patient safety, such as to prevent charging induced temperature rises above a threshold level suitable for a patient. For example, the base module can include a base module temperature sensor configured to output a base module temperature signal to the base module controller indicative of a temperature of the base module. The base module controller can be configured to control charging of the one or more base module battery cells based on the base module temperature signal feedback. Each of the plurality of external battery modules can include a temperature sensor configured to output a temperature signal to the controller of the external battery module indicative of a temperature of the external battery module. The controller of each of the plurality of battery modules can be configured to control charging of the one or more battery cells of the external battery module based on the temperature signal feedback. Charging can also be limited based on the amount of power available from the external power source(s).

In another aspect, a method is provided for supplying power to a medical device worn by a user or implanted in the user. The method includes supplying electrical power to the medical device via a base module that includes a base module input connector. Electrical power is supplied to the base module from a first external battery module via the base module input connector. The first external battery module includes one or more first battery cells, a first output connector, a first controller, and a first input connector. The one or more first battery cells are configured to store electrical power. The first output connector is operatively connected with the base module input connector to transfer electrical power to the base module. Electrical power is supplied to the first external battery module from a second external battery module via the first input connector. The second external battery module includes one or more second battery cells, a second output connector, a second controller, and a second input connector. The one or more second battery cells are configured to store electrical power. The second output connector is operatively connected with the first input connector to transfer electrical power to the first external battery module. Distribution of electrical power received by the first input connector from the second output connector is controlled, via the first controller, to charge the one or more first battery cells and/or to be output from the first output connector to the base module.

In many embodiments of the method, the base module includes one or more base module battery cells configured to store power and a base module controller. Distribution of electrical power received by the base module input connector from the first output connector can be controlled, via the base module controller, to charge the one or more base module battery cells and/or to be output to the medical device.

In many embodiments of the method, one or more signals are transferred to communicate connection of one or more of the external battery modules. For example, the method can include transferring a first signal from the second external battery module to the first external battery module indicating connection of the second external battery module to the first external battery module. The method can include transferring a second signal from the first external battery module to the base module indicating connection of the first external battery module to the base module and connection of the second external battery module to the first external battery module. The method can include controlling, by the base module controller, the distribution of electrical power received via the input connector of at least one of the plurality of external battery modules to charge the one or more battery cells of the respective external battery module and/or to be output via the output connector of the respective external battery module. The method can include implementing a charging sequence in which the base module is charged first and the first external battery module is charged after the base module is charged.

In many embodiments of the method, charging is controlled for patient safety, such as to prevent charging induced temperature rises above a threshold level suitable for a patient. For example, the method can include generating a base module temperature signal indicative of a temperature of the base module. Charging of the one or more base module battery cells can be controlled, via the base module controller, based on the base module temperature signal feedback to prevent a charging induced exceedance of a predetermined base module temperature. The method can include generating a first external battery module temperature signal indicative of a temperature of the first external battery module. Charging of the one or more first battery cells can be controlled, via the first controller, based on the first external battery temperature signal feedback to prevent a charging induced exceedance of a predetermined first external battery module temperature.

In many embodiments of the method, charge level of the base module and/or the external battery modules are monitored and communicated via the base module controller. For example, the method can include monitoring a base module charge level of the one or more base module battery cells. The base module charge level can be communicated to the user or a person other than the user. The base module charge level can be communicated to the user or a person other than the user by wirelessly transmitting the base module charge level to an electronic device, such as a cellular phone, for communication to the user or the person other than the user. The method can include monitoring, via the first controller, a first charge level of the one or more first battery cells. The first charge level can be communicated to the base module controller. The method can include monitoring, via the second controller, a second charge level of the one or more second battery cells. The second charge level can be communicated to the base module controller. The first and second charge levels can be communicated, via the base module controller, to the user or the person other than the user. Communicating the first and second charge levels to the user or the person other than the user can include wireless transmitting the first and second charge levels to an electronic device for communication to the user or the person other than the user.

In many embodiments of the method, the charge level of each of the external battery modules is monitored and communicated via the respective external battery module. For example, the method can include monitoring, via the first controller, a charge level of the one or more first battery cells. The charge level of the one or more first battery cells can be indicated via an indicator included in the first external battery module. The method can include monitoring, via the second controller, a charge level of the one or more second battery cells. The charge level of the one or more second battery cells can be indicated via an indicator included in the second external battery module.

The method can include supplying electrical power via one or more additional external battery modules. For example, the method can include supplying electrical power to the second external battery module from a third external battery module via the second input connector. The third external battery module can include one or more third battery cells, a third output connector, a third controller, and a third input connector. The one or more third battery cells are configured to store electrical power. The third output connector can be operatively connected with the second input connector to transfer electrical power to the second external battery module. The method can include controlling, via the second controller, distribution of electrical power received by the second input connector from the third output connector to charge the one or more second battery cells and/or to be output from the second output connector to the first external battery module.

The above presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented below.

For a fuller understanding of the nature and advantages of the present invention, reference should be made to the ensuing detailed description and accompanying drawings.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Figure 1:
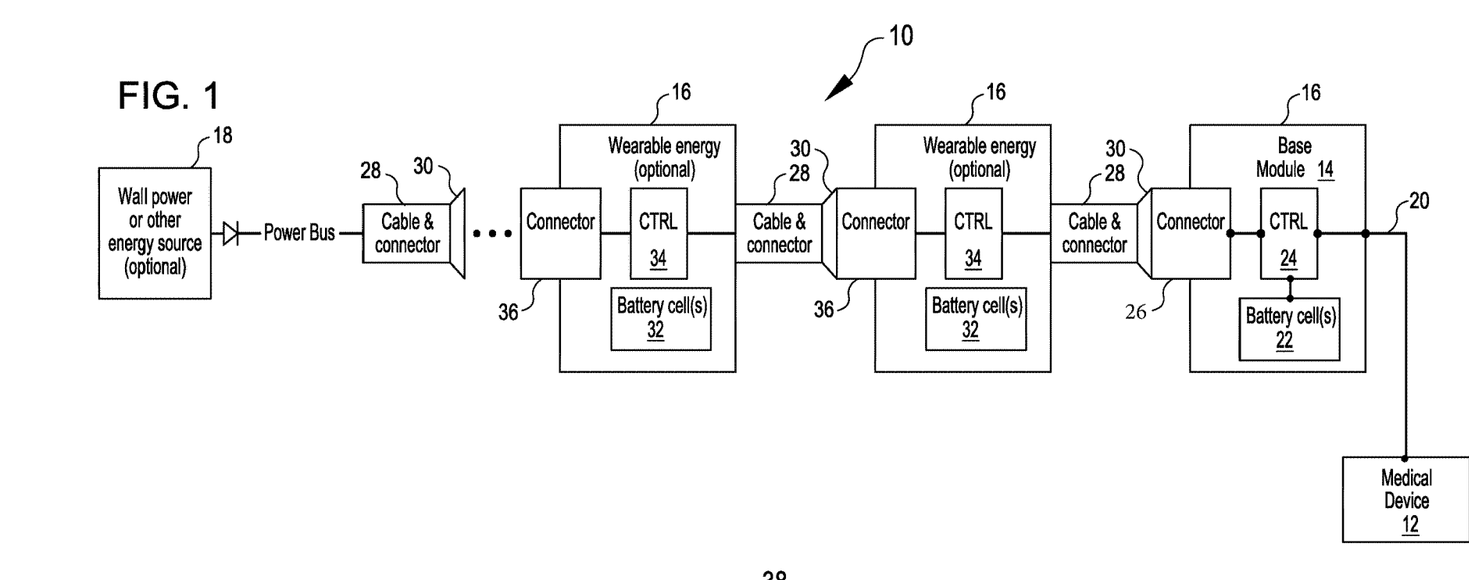
FIG. 1 is a simplified schematic diagram illustrating a system, in accordance with many embodiments, for supplying power to a medical device worn by a user or implanted in the user.

Referring now to the drawings, in which like reference numerals represent like parts throughout the several views, FIG. 1 shows a system 10, in accordance with many embodiments, for supplying power to a medical device worn by a user or implanted in the user. The system 10 includes a wearable or implantable medical device 12, a base module 14, a plurality of external battery modules 16, and a non-worn energy source 18. The external battery modules 16 are configured for selective serial connection to enable the connection of any suitable number of the external battery modules 16 to the base module 14 to vary the total battery capacity worn by the user. The non-worn energy source 18 can be any suitable energy source, for example, a wall power unit configured to convert utility power (e.g., 110 volt AC power) to direct current having a voltage level compatible with the external battery modules 16 and the base module 14. The non-worn energy source 18 can be selectively and intermittently connected to the most distal external battery module 16 to supply electrical power used to recharge the external battery modules 16, recharge the base module 14, and/or be output to the medical device 12 via a connection line 20.

The base module 14 is configured to supply operating electrical power to the medical device 12 via the connection line 20. The base module 14 includes one or more base module battery cells 22, a base module controller 24, and a base module input connector 26. The base module controller 24 is configured to supply power to the medical device 12 output by the one or more base module battery cells 22 and/or received via the base module input connector 26. In many embodiments, the base module controller 24 includes an integrated charger for recharging the one or more base module battery cells 22 via electrical power received via the base module input connector 26. In many embodiments, the base module controller 24 is configured to detect when at least one external battery module 16 or the non-worn energy source 18 is connected to the base module input connector 26. For example, the base module input connector 26 can include a data connection to receive a signal when at least one external battery module 16 or the non-worn energy source 18 is connected to the base module input connector 26. Alternatively, the base module controller 24 can be configured to detect when a suitable voltage potential is applied to the base module input connector 26 indicative of at least one external battery module 16 or the non-worn energy source 18 being connected to the base module input connector 26. When the connection of at least one of the external battery modules 16 or the non-worn energy source 18 to the base module input connector 26 is detected, the base module controller 24 can supply electrical power to the medical device solely via electrical power received via the base module input connector 26 and can simultaneously recharge the one or more base module battery cells 22 via electrical power received via the base module input connector 26 if the one or more base module battery cells 22 are not already fully charged. When the base module controller 24 does not detect the connection of any power source to the base module input connector 24, the base module controller 24 is configured to supply electrical power to the medical device 12 via electrical power from the one or more base module battery cells 22.

In the illustrated embodiment, each of the external battery modules 16 includes an output cable 28, an output connector 30, one or more external battery cells 32, an external battery controller 34, and an input connector 36. The external battery controller 34 is configured to supply power via the output connector 30 output by the one or more external battery cells 32 and/or received via the input connector 36. In many embodiments, the external battery controller 34 includes an integrated charger for recharging the one or more external battery cells 32 via electrical power received via the input connector 36. In many embodiments, the external battery controller 34 is configured to detect when at least one external battery module 16 or the non-worn energy source 18 is connected to the input connector 36. For example, the input connector 36 can include a data connection to receive a signal when at least one external battery module 16 or the non-worn energy source 18 is connected to the input connector 26. Alternatively, the external battery controller 34 can be configured to detect when a suitable voltage potential is applied to the input connector 36 indicative of at least one external battery module 16 or the non-worn energy source 18 being connected to the input connector 36. When the connection of at least one of the external battery modules 16 or the non-worn energy source 18 to the input connector 36 is detected, the external battery controller 34 can supply electrical power via the output connector 30 via electrical power received via the input connector 36 and can simultaneously recharge the one or more external battery cells 32 via electrical power received via the input connector 36 if the one or more external battery cells 32 are not already fully charged. When the external battery controller 34 does not detect the connection of any power source to the input connector 34, the external battery controller 34 is configured to output electrical power via the output connector 30 via electrical power from the one or more external battery cells 32.

Any suitable serial combination of the external battery modules 16 can be used. For example, zero, one, two, three, four, or greater of the external battery modules 16 can be serially connected to the base module 14 to supply power to the base module 14 for supply to the medical device 12. Additionally, in many embodiments, the non-worn power source 18 can be connected directly to the base module 14 to supply electrical power that can be used by the base module 14 to supply electrical power to the medical device 12 and to recharge the one or more base module battery cells 22 if the one or more base module battery cells 22 are not already fully charged. While the external battery modules 16 are configured to be serially connected physically, the external battery modules 16 are configured so as to be connected in parallel electrically so as to not vary the voltage supplied to the base module 14.

Figure 2:
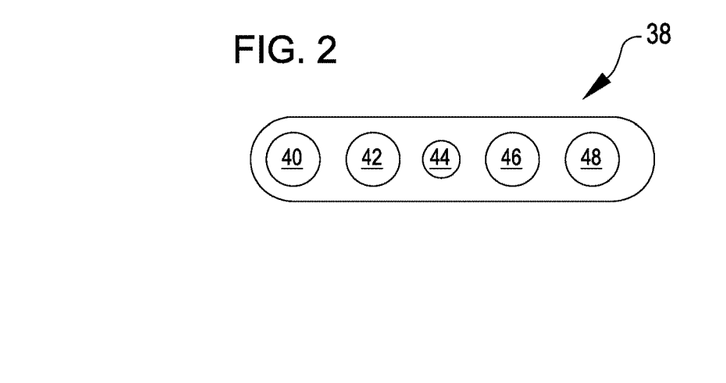
FIG. 2 illustrates an embodiment of a connector that can be used in the system of FIG. 1.

FIG. 2 shows a connector arrangement 38 that can be used in the base module input connector 26, the output connector 30, and the input connector 36. The connector arrangement 38 includes two first power connectors 40, two second power connectors 42, and a data connector 44. The first and the second connectors 40, 42 are used to transfer power. For example, each of the first connectors 40 can be electrically connected to a power lead and each of the second connectors 42 can be electrically connected to a ground lead, and vice-versa. The data connector 44 is used to connect data lines to transmit data between the base module controller 24 and the one or more external battery controllers 34 and/or between any of the one or more external battery controllers 34. In optional embodiments, the data connector 44 can be omitted, for example, in embodiments where connection of an external battery module 16 to either the base module input connector 26 or to the input connector 36 of another external battery module 16 is detected via detection of voltage potential applied via the first and second connectors 40, 42. The symmetrical arrangement of the connectors 40, 42, 44 accommodates connection of the connector arrangement 38 in opposite orientations, thereby accommodating proper connection in either of the two possible orientations between connectors.

Figure 3:
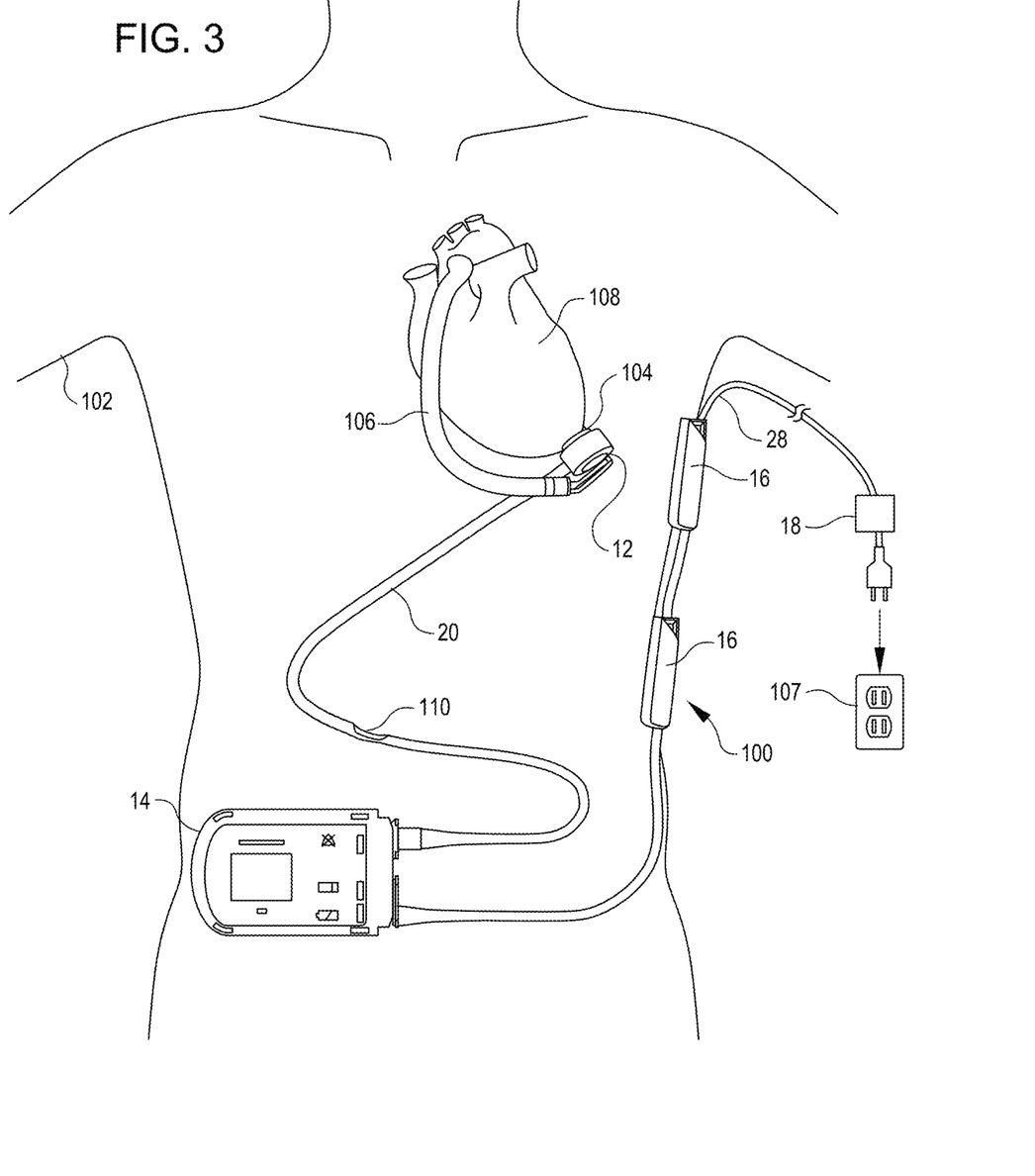
FIG. 3 illustrates an example medical device system that employs the system of FIG. 1.

The system 10 can be employed in any suitable medical system (e.g., a worn or at least partially implanted medical system). For example, FIG. 3 illustrates a mechanical circulatory support system 100 that employs the system 10. The mechanical circulatory support system 100 includes an implantable blood pump assembly (i.e., medical device 12) implanted in a patient 102, a ventricular cuff 104, an outflow cannula 106, and an external system controller (base module 14). In the illustrated configuration, two of the external battery modules 16 are shown serially connected to the external system controller 14. As described herein, however, any suitable number of the external battery modules 16 and/or the non-worn energy source 18 (e.g., that can be powered via being plugged into an outlet 107) can be coupled with the external system controller 14 to supply power to the external system controller 14 for supply to the blood pump assembly 12. The blood pump assembly 12 can include a VAD that is attached to an apex of the left ventricle, as illustrated, or the right ventricle, or both ventricles of the patient's heart 108. The VAD can include a centrifugal pump (as shown) that is capable of pumping the entire output delivered to the left ventricle from the pulmonary circulation (i.e., up to 10 liters per minute). Related blood pumps applicable to the present invention are described in greater detail below and in U.S. Pat. Nos. 5,695,471, 6,071,093, 6,116,862, 6,186,665, 6,234,772, 6,264,635, 6,688,861, 7,699,586, 7,976,271, 7,997,854, 8,007,254, 8,152,493, 8,652,024, and 8,668,473 and U.S. Patent Publication Nos. 2007/0078293, 2008/0021394, 2009/0203957, 2012/0046514, 2012/0095281, 2013/0096364, 2013/0170970, 2013/0121821, and 2013/0225909, all of which are incorporated herein by reference for all purposes in their entirety. The blood pump assembly 12 can be attached to the heart 108 via the ventricular cuff 104, which can be sewn to the heart 108 and coupled to the blood pump 12. The other end of the blood pump 12 connects to the ascending aorta via the outflow cannula 106 so that the VAD effectively diverts blood from the weakened ventricle and propels it to the aorta for circulation through the rest of the patient's vascular system.

FIG. 3 illustrates the mechanical circulatory support system 100 during battery powered operation by the system 10 via the two connected external battery modules 16. A driveline (connection line 20) that exits through the patient's abdomen 110 connects the implanted blood pump assembly 12 to the external system controller 14, which monitors system 100 operation. Related controller systems applicable to the present invention are described in greater detail below and in U.S. Pat. Nos. 5,888,242, 6,991,595, 8,323,174, 8,449,444, 8,506,471, 8,597,350, and 8,657,733, EP 1812094, and U.S. Patent Publication Nos. 2005/0071001 and 2013/0314047, all of which are incorporated herein by reference for all purposes in their entirety. As described herein the power system 10 used to power the system 100 can include any suitable combination (zero, one, two, three, four, or more) of the external battery modules 16 and/or the non-worn power source 18.

Figure 4:
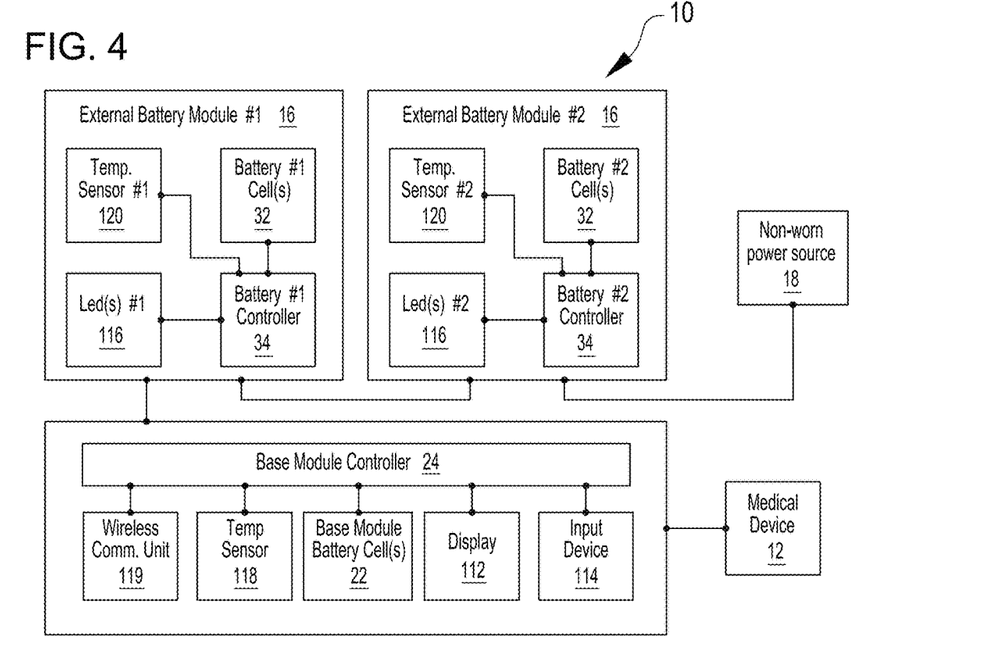
FIG. 4 is a simplified schematic diagram illustrating components of an embodiment of the system of FIG. 1.

FIG. 4 is a simplified schematic diagram illustrating components of an embodiment of the system 10. In the illustrated configuration, the base module 14 is operatively coupled with the medical device 12 and a combination of two external battery modules 16 and the non-worn power source 18 are connected to the base module 14 to supply power to the base module 14. Description of aspects of the system 10 already described above are not repeated here. Additional aspects of the base module 14 and the external battery modules 16 are described below.

In the embodiment shown in FIG. 4, the system 10 is configured to monitor and display the charge level of the one or more base module battery cells 22 and/or the one or more external battery cells 32 in each of the external battery modules 16. In the illustrated embodiment, the base module 14 includes a display 112 and an input device 114 and each of the external battery modules 16 include one or more indicator lights (e.g., LED(s) 116). The base module controller 24 can be configured to monitor the charge level of the one or more base module battery cells 22 and output the charge level of the one or more base module battery cells 22 via the display 112. Each of the battery controllers 34 can be configured to monitor the charge level of the one or more external battery cells 32 and transmit the charge level to the base module 14 and/or output an indication of the charge level via operation of the LED(s) 116. For example, the external battery module 16 having the lowest state of charge of the one or more external battery cells 32 (typically the most distal of the serially connected chain of external battery modules 16) can operate the LED(s) 116 to indicate the state of charge (e.g., flashing either red or green based on the charge level). One or more indicators can be displayed on the display 112 suitable to communicate the charge state of the one or more base module battery cells 22 an/or the charge state of the one or more external battery cells 32 in each of the external battery modules 16. For example, a bell shaped indicator can be displayed to output a lower priority notification regarding power level of the batteries. One or more battery shaped indicators can be used to display the charge level of the one or more base module battery cells 22 and/or the state of charge of any suitable number of the connected external battery modules 16. For example, the display 112 can be configured to display the charge level of the one or more base module battery cells 22 via a first battery shaped indicator and display the lowest charge level of the connected external battery modules 16 via a second battery shaped indicator. In the illustrated embodiment, the base module 14 includes a wireless communication unit 119 configured to wirelessly transmit the charge level of the base module 14 and/or the charge level of any suitable combination of the external battery modules 16 to an electronic device, such as a cellular/smart phone, tablet, computer, watch, etc., for communication to the user or a person other than the user (e.g., physician, family member, etc.).

Additionally, in the embodiment shown in FIG. 4, the system 10 is configured to control charging to avoid charging induced excessive temperature of the base module 14 and the external battery modules 16. The base module 14 includes a temperature sensor 118 that outputs a temperature signal to the base module controller 24 indicative of a temperature of the base module 14. The base module controller 24 is configured to control the rate at which the one or more base module battery cells 22 are charged based on the temperature signal from the temperature sensor 118 to prevent having the temperature sensed by the temperature sensor 118 exceed a suitable limit with regard to patient contact with the base module 14. Similarly, each of the external battery modules 16 includes a temperature sensor 120 that outputs a temperature signal to the external battery module controller 34 indicative of a temperature of the external battery module 16. The external battery module controller 34 is configured to control the rate at which the one or more external battery cells 32 are charged based on the temperature signal from the temperature sensor 120 to prevent having the temperature sensed by the temperature sensor 120 exceed a suitable limit with regard to patient contact with the external battery module 16.

While the external battery modules 16 are serially-connected physically, the external battery modules 16 are electrically coupled in parallel. In many embodiments, the base module controller 24 and the external battery module controllers 34 include electronically controlled switches (e.g., metal-oxide-semiconductor field-effect transistors (MOSFETs)) that are used to control distribution of electrical power received via the respective input connector to be output via the respective output connector and used to charge the respective one or more battery cells if not already fully charged.

Figure 5:
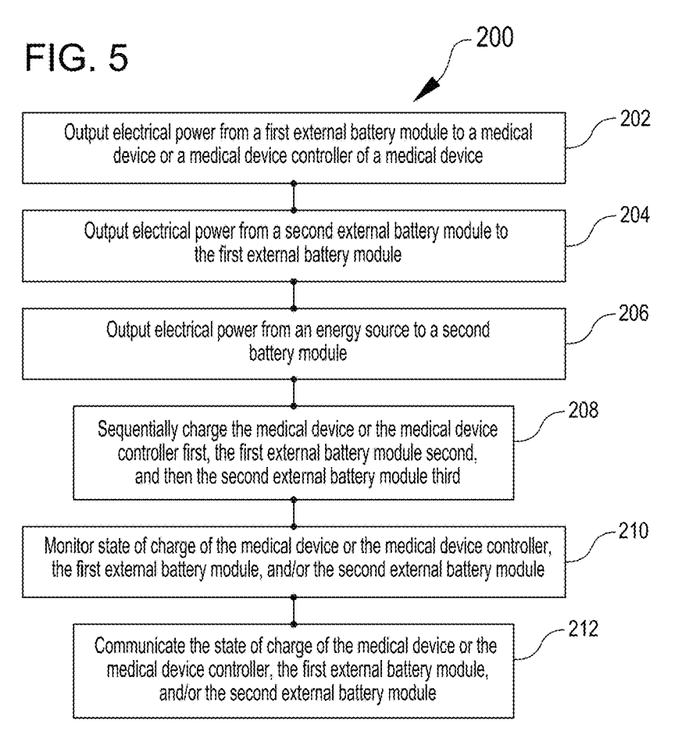
FIG. 5 is a simplified block diagram of acts of a method, in accordance with many embodiments, for supplying power to a medical device worn by a user or implanted in the user.

FIG. 5 is a simplified block diagram of acts of a method 200, in accordance with many embodiments, for supplying power to a medical device worn by a user or implanted in the user. Any suitable external battery system can be used to practice the method 200, including the systems described herein. The method 200 can include any suitable combination of a set of subset of the following: (1) outputting electrical power from a first external battery module to a medical device or a medical device controller of a medical device (act 202); (2) outputting electrical power from a second external battery module to the first external battery module (act 204); (3) outputting electrical power from an energy source to the second external battery module (act 206); (4) Sequentially charging the medical device or the medical device controller first, the first external battery module second, and then the second external battery module third (act 208); (5) monitoring state of charge of the medical device or the medical device controller, the first external battery module, and/or the second external battery module (act 210); and (6) communicating the state of charge of the medical device or the medical device controller, the first external battery module, and/or the second external battery module (act 212).

Figure 6:
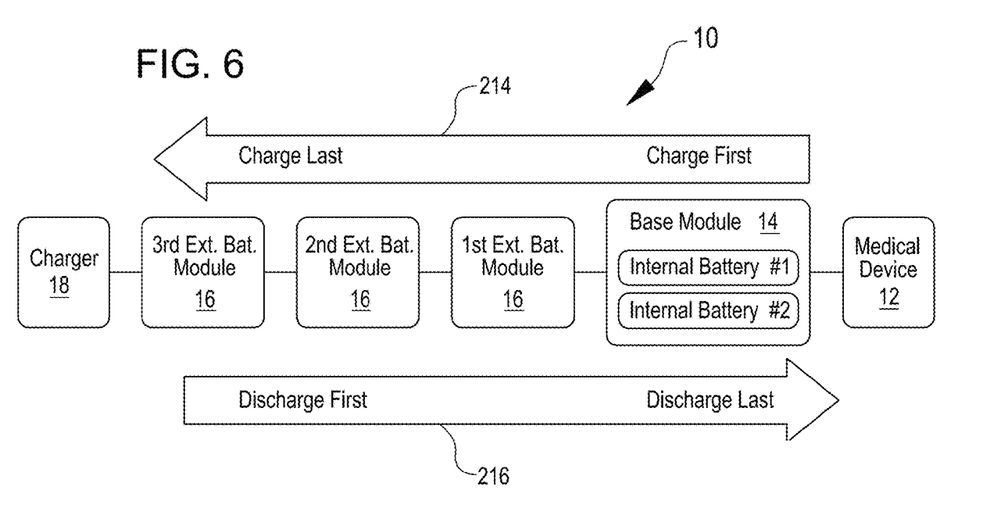
FIG. 6 is a simplified schematic diagram of a charging sequence and a discharging sequence that can be employed in a medical device system, in accordance with many embodiments.

FIG. 6 is a simplified schematic diagram of a charging sequence 214 and a discharging sequence 216 that can be employed in the medical device system 10, in accordance with many embodiments. In the illustrated configuration in which a charger 18 is connected, the power supplied by the charger 18 can be used to charge the base module 14 first. When the base module 14 is fully charged, the power supplied by the charger 18 can be used to charge the first external battery module 16. When the first external battery module 16 is fully charged, the power supplied by the charger 18 can be used to charge the second external battery module 16. And finally, when the second external battery module is fully charged, the power supplied by the charger can be used to charge the third external battery module 16. When the charger 18 is disconnected, the medical device 12 can be run first via power supplied by the third external battery module 16, thereby discharging the third external battery module 16 first. When the third external battery module 16 is effectively discharged, the medical device can be run second via power supplied by the second battery module 16, thereby discharging the second external battery module 16 second. When the second external battery module 16 is effectively discharged, the medical device can be run third via power supplied by the first battery module 16, thereby discharging the first external battery module 16 third. When the first external battery module 16 is effectively discharged, the medical device can be run last via power supplied by the base module 14, thereby discharging the base module 14 last.

A combination of the charging sequence 214 and the discharging sequence 216 can be used at the same time when the charger 18 is not connected. For example, power supplied by the third external battery module 16, in addition to being used to power the medical device 12, can first be used to charge the base module 14 when the base module 14 is not already fully charged, and can then be used to charge the first external battery module 16 when the first external battery module 16 is not already fully charged, and can then be used to charge the second external battery module 16 when the second external battery module 16 is not already fully charged. A similar combination of the charging sequence 214 and the discharging sequence 216 can be used when only the first and second external battery modules 16 are connected to the base module 14 and when only the first external battery module 16 is connected to the base module 14.

The utility of the systems and methods disclosed herein can be understood through example embodiments. Consider a VAS controller with only two daisy-chained external battery modules connected. In one method of operation, the most distal external battery module discharges first so that it can be removed when depleted without disconnecting the other external battery module from the VAS controller. Once the most distal external battery module is disconnected, the user is then carrying less weight and bulk. In another method of operation, both of the external battery modules discharge evenly. In some embodiments, a preferred method of discharge behavior can be selected and the selection stored as a parameter in the VAS controller and passed to the connected battery modules. In some embodiments, a preferred method of charge behavior can be selected and the selection stored as a parameter in the VAS controller and passed to the connected battery modules.

In addition to the approaches described above, any suitable method can be used for charging the battery modules. For example, one method is for the external battery modules to disable recharging unless an AC power source is connected at the distal end of the daisy-chained battery modules. Another method is for the distal most battery module or modules to recharge the innermost battery module in addition to providing power to the VAS. A combination of these first two methods is to sequentially charge the innermost battery module when AC power is present or allow some set of the battery modules in the daisy-chain to charge simultaneously. As described herein, charging rate can be limited to avoid temperature exceedance(s) with respect to regulatory requirements for the surface temperature of devices in proximity to humans. Overall charging levels may also be limited by the size of the power cables used. Charging rate can also be controlled to prevent temperature exceedance(s) via logic embodied within each battery that knows a priori how much heat is generated for a given charge current at a given state of charge. The logic can further modulate the charge current based on temperature sensors placed near the surface of the external battery module. The logic can communicate the charge current level to the VAS controller. The VAS controller, knowing the charge level commanded by all daisy-chained battery packs, can scale or otherwise change individual charge currents based on system level considerations or user preferences.

To further illustrate, consider three external battery modules daisy-chained to a VAS controller. Based on a user preference to keep the innermost battery module fully charged at all times, the VAS controller can send a message to the innermost battery module to begin charging. The VAS controller can also send messages to the outer battery modules to not charge and for the outermost battery module to preferentially discharge first. The outermost battery module then discharges fully. When the outermost battery module is depleted of energy, the penultimate pack begins discharging—providing power to the medical device and, if still necessary, to continue charging the innermost battery module. During this time, if the temperature sensor(s) inside the innermost battery module measure a surface temperature nearing its maximum allowable limit, the innermost battery module can reduce the charge current per a local control feedback algorithm and communicates this condition to the VAS controller.

Other variations are within the spirit of the present invention. For example, the medical device 12 and the base module 14 can be combined in a single unit such as, for example, in the case of a wearable medical device. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A system for supplying power to a medical device worn by a user or implanted in the user, the system comprising:
   a medical device configured to be worn by a user or implanted in the user;
   a connection line configured to be operatively coupled with the medical device, wherein the connection line is configured for transmission of electrical power to the medical device to power operation of the medical device;
   a base module configured to be operatively coupled with the medical device via the connection line to supply electrical power through the connection line to the medical device, wherein the base module is configured to control operation of the medical device and includes a base module input connector; and
   external battery modules, each of the external battery modules including:
      one or more battery cells configured to store electrical power;
      an output connector configured to output electrical power from the external battery module and to the base module;
      an input connector configured to receive electrical power from another of the external battery modules; and
      a controller configured to control distribution of electrical power received via the input connector to charge the one or more battery cells and/or to be output via the output connector.

2. The system of claim 1, wherein the base module includes:
one or more base module battery cells configured to store electrical power; and
a base module controller configured to control distribution of electrical power received via the base module input connector to charge the one or more base module battery cells and/or to be output to the connection line to supply electrical power to the medical device.

3. The system of claim 2, wherein each of the base module input connector, the output connector of each of the external battery modules, and the input connector of each of the external battery modules comprises a data connection for transferring a connection signal to the base module and/or to the controller of another of the external battery modules indicating connection of one or more of the external battery modules.

4. The system of claim 3, wherein:
the base module controller is configured to monitor a base module charge level of the one or more base module battery cells; and
the base module controller is configured to indicate the base module charge level to the user or a person other than the user.

5. The system of claim 4, wherein:
the controller of each of the external battery modules is configured to monitor a charge level of the one or more battery cells of the external battery module and communicate the charge level to the base module controller; and
the base module controller is configured to communicate the charge level of at least one of the external battery modules to the user or a person other than the user.

6. The system of claim 3, wherein the base module controller is configured to control the controller of each of the external battery modules via the data connection to control the distribution of electrical power received via the input connector of the external battery module to charge the one or more battery cells of the external battery module and/or to be output via the output connector of the external battery module.

7. A method of supplying power to a medical device worn by a user or implanted in the user, the method comprising:
supplying electrical power to the medical device via a base module that includes a base module input connector, wherein the electrical power is transmitted through a connection line from the base module to the medical device;
controlling, by the base module, operation of the medical device;
supplying electrical power to the base module from a first external battery module via the base module input connector; the first external battery module including one or more first battery cells, a first output connector, a first controller, and a first input connector; the one or more first battery cells being configured to store electrical power, the first output connector being operatively connected with the base module input connector to transfer electrical power to the base module; and
supplying electrical power to the first external battery module from a second external battery module via the first input connector; the second external battery module including one or more second battery cells, a second output connector, a second controller, and a second input connector; the one or more second battery cells being configured to store electrical power, the second output connector being operatively connected with the first input connector to transfer electrical power to the first external battery module; and
controlling, via the first controller, distribution of electrical power received by the first input connector from the second output connector to charge the one or more first battery cells and/or to be output from the first output connector to the base module.

8. The method of claim 7, wherein the base module includes one or more base module battery cells configured to store power and a base module controller, the method further comprising controlling, via the base module controller, distribution of electrical power received by the base module input connector from the first output connector to charge the one or more base module battery cells and/or to be output to the medical device.

9. The method of claim 8, further comprising:
transferring a first connection signal from the second external battery module to the first external battery module indicating connection of the second external battery module to the first external battery module; and
transferring a second connection signal from the first external battery module to the base module indicating connection of the first external battery module to the base module and connection of the second external battery module to the first external battery module.

10. The method of claim 8, further comprising controlling, by the base module controller, the distribution of electrical power received via the input connector of at least one of the first and second external battery modules to charge the one or more battery cells of the respective external battery module and/or to be output via the output connector of the respective external battery module.

11. The method of claim 8, further comprising implementing a charging sequence in which the base module is charged first and the first external battery module is charged after the base module is charged.

12. The method of claim 8, further comprising:
generating a base module temperature signal indicative of a temperature of the base module; and
controlling, via the base module controller, charging of the one or more base module battery cells based on the base module temperature signal to prevent a charging induced exceedance of a predetermined base module temperature.

13. The method of claim 8, further comprising:
monitoring a base module charge level of the one or more base module battery cells; and
communicating the base module charge level to the user or a person other than the user.

14. The method of claim 13, wherein communicating the base module charge level to the user or a person other than the user comprises wirelessly transmitting the base module charge level to an electronic device for communication to the user or the person other than the user.

15. The method of claim 8, further comprising:
monitoring, via the first controller, a first charge level of the one or more first battery cells;
communicating the first charge level to the base module controller;
monitoring, via the second controller, a second charge level of the one or more second battery cells;
communicating the second charge level to the base module controller; and
communicating, via the base module controller, the first and second charge levels to the user or a person other than the user.

16. The method of claim 15, wherein communicating the first and second charge levels to the user or the person other than the user comprises wireless transmitting the first and second charge levels to an electronic device for communication to the user or the person other than the user.

17. The method of claim 7, further comprising:
generating a first external battery module temperature signal indicative of a temperature of the first external battery module; and
controlling, via the first controller, charging of the one or more first battery cells based on the first external battery temperature signal to prevent a charging induced exceedance of a predetermined first external battery module temperature.

18. The method of claim 7, further comprising:
monitoring, via the first controller, a charge level of the one or more first battery cells;
indicating, via an indicator included in the first external battery module, the charge level of the one or more first battery cells;
monitoring, via the second controller, a charge level of the one or more second battery cells; and
indicating, via an indicator included in the second external battery module, the charge level of the one or more second battery cells.

19. The method of claim 7, further comprising:
supplying electrical power to the second external battery module from a third external battery module via the second input connector; the third external battery module including one or more third battery cells, a third output connector, a third controller, and a third input connector; the one or more third battery cells being configured to store electrical power, the third output connector being operatively connected with the second input connector to transfer electrical power to the second external battery module; and
controlling, via the second controller, distribution of electrical power received by the second input connector from the third output connector to charge the one or more second battery cells and/or to be output from the second output connector to the first external battery module.

20. The method of claim 7, further comprising:
discharging the one or more second battery cells to transfer electrical power stored in the one or more second battery cells to the first external battery module; and
controlling distribution of the electrical power discharged from the one or more second battery cells and transferred to the first external battery module to simultaneously output electrical power via the first output connector to the base module and charge the one or more first battery cells.

\* \* \* \* \*